US008906057B2

(12) United States Patent
Connor et al.

(10) Patent No.: US 8,906,057 B2
(45) Date of Patent: Dec. 9, 2014

(54) ANEURYSM EMBOLIZATION BY ROTATIONAL ACCUMULATION OF MASS

(75) Inventors: Robert A. Connor, Minneapolis, MN (US); Muhammad Tariq Janjua, Inver Grove Heights, MN (US)

(73) Assignee: Aneuclose LLC, Forest Lake, MN (US)

( * ) Notice: Subject to any disclaimer, the term of this patent is extended or adjusted under 35 U.S.C. 154(b) by 562 days.

(21) Appl. No.: 12/930,303

(22) Filed: Jan. 3, 2011

(65) Prior Publication Data

US 2011/0166588 A1   Jul. 7, 2011

Related U.S. Application Data

(60) Provisional application No. 61/335,257, filed on Jan. 4, 2010.

(51) Int. Cl.
*A61M 29/00* (2006.01)
*A61M 25/00* (2006.01)
*A61B 17/12* (2006.01)
*A61B 17/00* (2006.01)

(52) U.S. Cl.
CPC .......... *A61M 25/00* (2013.01); *A61B 17/12113* (2013.01); *A61B 17/1214* (2013.01); *A61M 25/0082* (2013.01); *A61B 2017/003* (2013.01); *A61B 2017/00557* (2013.01); *A61B 2017/00867* (2013.01); *A61B 2017/12054* (2013.01); *A61B 2017/12068* (2013.01); *A61B 2017/12072* (2013.01)
USPC ........... 606/200; 606/145; 606/146; 606/191; 606/194

(58) Field of Classification Search
CPC ..................... A61B 17/12113; A61B 17/1214; A61B 17/12031
USPC ............. 606/32–33, 157, 191, 194, 200, 213, 606/215; 128/831, 841
See application file for complete search history.

(56) References Cited

U.S. PATENT DOCUMENTS

| | | |
|---|---|---|
| 5,334,210 A | 8/1994 | Gianturco |
| 5,382,259 A | 1/1995 | Phelps et al. |
| 5,522,822 A | 6/1996 | Phelps et al. |
| 5,645,559 A | 7/1997 | Hachtman et al. |
| 5,690,666 A | 11/1997 | Berenstein et al. |
| 5,718,711 A | 2/1998 | Berenstein et al. |
| 5,723,004 A | 3/1998 | Dereume et al. |
| 5,749,891 A * | 5/1998 | Ken et al. ................. 606/200 |
| 5,749,894 A | 5/1998 | Engelson |
| 5,766,219 A | 6/1998 | Horton |
| 5,769,882 A | 6/1998 | Fogarty et al. |
| 5,769,884 A | 6/1998 | Solovay |
| 5,861,003 A | 1/1999 | Latson et al. |
| 5,916,235 A | 6/1999 | Guglielmi |

(Continued)

FOREIGN PATENT DOCUMENTS

WO   WO 2008013869 A2 *   1/2008

*Primary Examiner* — Darwin Erezo
*Assistant Examiner* — Kendra Obu (57) ABSTRACT

This invention is a device and method for reducing blood flow into an aneurysm, especially a cerebral aneurysm, in order to promote therapeutic embolization of the aneurysm. The device comprises: at least one core member that is inserted into the aneurysm; and at least one longitudinal flexible member that is wound repeatedly around the core member within the aneurysm. The longitudinal flexible member is wound around the core member until the rotational accumulation of the flexible member reduces blood flow into the aneurysm and promotes therapeutic embolization of the aneurysm.

13 Claims, 9 Drawing Sheets

(56) References Cited

U.S. PATENT DOCUMENTS

| | | |
|---|---|---|
| 5,928,260 A | 7/1999 | Chin et al. |
| 5,941,249 A | 8/1999 | Maynard |
| 5,948,018 A | 9/1999 | Dereume et al. |
| 5,951,599 A | 9/1999 | McCrory |
| 5,976,162 A | 11/1999 | Doan et al. |
| 6,024,754 A | 2/2000 | Engelson |
| 6,063,111 A | 5/2000 | Hieshima et al. |
| 6,096,034 A | 8/2000 | Kupiecki et al. |
| 6,139,564 A | 10/2000 | Teoh |
| 6,165,193 A | 12/2000 | Greene et al. |
| 6,165,212 A | 12/2000 | Dereume et al. |
| 6,168,592 B1 | 1/2001 | Kupiecki et al. |
| 6,168,622 B1 | 1/2001 | Mazzocchi |
| 6,193,708 B1 * | 2/2001 | Ken et al. ............... 606/1 |
| 6,270,523 B1 | 8/2001 | Herweck et al. |
| 6,299,619 B1 | 10/2001 | Greene et al. |
| 6,309,367 B1 | 10/2001 | Boock |
| 6,309,413 B1 | 10/2001 | Dereume et al. |
| 6,331,191 B1 | 12/2001 | Chobotov |
| 6,342,068 B1 | 1/2002 | Thompson |
| 6,344,041 B1 | 2/2002 | Kupiecki et al. |
| 6,344,048 B1 | 2/2002 | Chin et al. |
| 6,346,117 B1 | 2/2002 | Greenhalgh |
| 6,350,270 B1 | 2/2002 | Roue |
| 6,375,668 B1 | 4/2002 | Gifford et al. |
| 6,391,037 B1 | 5/2002 | Greenhalgh |
| 6,409,749 B1 | 6/2002 | Maynard |
| 6,428,558 B1 | 8/2002 | Jones et al. |
| 6,454,780 B1 | 9/2002 | Wallace |
| 6,500,190 B2 | 12/2002 | Greene et al. |
| 6,506,204 B2 | 1/2003 | Mazzocchi |
| 6,547,804 B2 | 4/2003 | Porter et al. |
| 6,569,190 B2 | 5/2003 | Whalen et al. |
| 6,585,748 B1 | 7/2003 | Jeffree |
| 6,602,261 B2 | 8/2003 | Greene et al. |
| 6,605,111 B2 | 8/2003 | Bose et al. |
| 6,613,074 B1 | 9/2003 | Mitelberg et al. |
| 6,626,928 B1 | 9/2003 | Raymond et al. |
| 6,656,214 B1 | 12/2003 | Fogarty et al. |
| 6,673,103 B1 | 1/2004 | Golds et al. |
| 6,723,108 B1 | 4/2004 | Jones et al. |
| 6,746,468 B1 | 6/2004 | Sepetka et al. |
| 6,770,087 B2 | 8/2004 | Layne et al. |
| 6,780,196 B2 | 8/2004 | Chin et al. |
| 6,786,920 B2 | 9/2004 | Shannon et al. |
| 6,790,225 B1 | 9/2004 | Shannon et al. |
| 6,802,851 B2 | 10/2004 | Jones et al. |
| 6,811,560 B2 | 11/2004 | Jones et al. |
| 6,855,153 B2 | 2/2005 | Saadat |
| 6,855,154 B2 | 2/2005 | Abdel-Gawwad |
| 6,958,061 B2 | 10/2005 | Truckai et al. |
| 6,960,217 B2 | 11/2005 | Bolduc |
| 6,979,344 B2 | 12/2005 | Jones et al. |
| 7,029,487 B2 | 4/2006 | Greene et al. |
| 7,052,513 B2 | 5/2006 | Thompson |
| 7,070,609 B2 | 7/2006 | West |
| 7,083,632 B2 | 8/2006 | Avellanet et al. |
| 7,083,643 B2 | 8/2006 | Whalen et al. |
| 7,153,323 B1 | 12/2006 | Teoh et al. |
| 7,156,871 B2 | 1/2007 | Jones et al. |
| 7,186,263 B2 | 3/2007 | Golds et al. |
| 7,201,762 B2 | 4/2007 | Greene, Jr. et al. |
| 7,211,109 B2 | 5/2007 | Thompson |
| 7,229,461 B2 | 6/2007 | Chin et al. |
| 7,303,571 B2 | 12/2007 | Makower et al. |
| 7,306,622 B2 | 12/2007 | Jones et al. |
| 7,306,624 B2 | 12/2007 | Yodfat et al. |
| 7,491,214 B2 | 2/2009 | Greene et al. |
| 7,520,893 B2 | 4/2009 | Rivelli |
| 7,569,066 B2 | 8/2009 | Gerberding |
| 7,753,931 B2 | 7/2010 | Diaz et al. |
| 7,766,871 B2 | 8/2010 | Hirszowicz et al. |
| 7,803,180 B2 | 9/2010 | Burpee et al. |
| 7,806,857 B2 | 10/2010 | Khosravi et al. |
| 2002/0042628 A1 | 4/2002 | Chin et al. |
| 2002/0169473 A1 | 11/2002 | Sepetka et al. |
| 2003/0083676 A1 | 5/2003 | Wallace |
| 2003/0093097 A1 | 5/2003 | Avellanet et al. |
| 2003/0135264 A1 | 7/2003 | Whalen et al. |
| 2003/0181927 A1 | 9/2003 | Wallace |
| 2003/0187473 A1 | 10/2003 | Berenstein et al. |
| 2003/0195553 A1 | 10/2003 | Wallace et al. |
| 2004/0098027 A1 | 5/2004 | Teoh et al. |
| 2004/0158282 A1 | 8/2004 | Jones et al. |
| 2004/0181253 A1 | 9/2004 | Sepetka et al. |
| 2005/0021077 A1 | 1/2005 | Chin et al. |
| 2005/0033349 A1 | 2/2005 | Jones et al. |
| 2005/0267510 A1 | 12/2005 | Razack |
| 2006/0052816 A1 | 3/2006 | Bates et al. |
| 2006/0058834 A1 | 3/2006 | Do et al. |
| 2006/0079923 A1 | 4/2006 | Chhabra et al. |
| 2006/0116709 A1 | 6/2006 | Sepetka et al. |
| 2006/0116712 A1 | 6/2006 | Sepetka et al. |
| 2006/0116713 A1 | 6/2006 | Sepetka et al. |
| 2006/0155323 A1 | 7/2006 | Porter et al. |
| 2006/0206139 A1 | 9/2006 | Tekulve |
| 2006/0235464 A1 | 10/2006 | Avellanet et al. |
| 2006/0276831 A1 | 12/2006 | Porter et al. |
| 2006/0292206 A1 | 12/2006 | Kim et al. |
| 2007/0038288 A1 | 2/2007 | Lye et al. |
| 2007/0050008 A1 | 3/2007 | Kim et al. |
| 2007/0055355 A1 | 3/2007 | Kim et al. |
| 2007/0078506 A1 | 4/2007 | McCormick et al. |
| 2007/0083226 A1 * | 4/2007 | Buiser et al. ............... 606/200 |
| 2007/0088387 A1 | 4/2007 | Eskridge et al. |
| 2007/0106311 A1 | 5/2007 | Wallace et al. |
| 2007/0150041 A1 | 6/2007 | Evans et al. |
| 2007/0150045 A1 | 6/2007 | Ferrera |
| 2007/0167747 A1 | 7/2007 | Borgert et al. |
| 2007/0168011 A1 | 7/2007 | LaDuca et al. |
| 2007/0207186 A1 | 9/2007 | Scanlon et al. |
| 2007/0219578 A1 | 9/2007 | Solar et al. |
| 2007/0219610 A1 | 9/2007 | Israel |
| 2007/0219619 A1 | 9/2007 | Dieck |
| 2007/0239191 A1 * | 10/2007 | Ramzipoor ............... 606/191 |
| 2007/0239261 A1 | 10/2007 | Bose et al. |
| 2007/0276469 A1 | 11/2007 | Tenne |
| 2007/0276470 A1 | 11/2007 | Tenne |
| 2008/0004653 A1 | 1/2008 | Sherman et al. |
| 2008/0033341 A1 | 2/2008 | Grad |
| 2008/0033480 A1 | 2/2008 | Hardert |
| 2008/0039933 A1 | 2/2008 | Yodfat et al. |
| 2008/0045996 A1 | 2/2008 | Makower et al. |
| 2008/0114391 A1 | 5/2008 | Dieck et al. |
| 2008/0114436 A1 | 5/2008 | Dieck et al. |
| 2008/0147100 A1 | 6/2008 | Wallace |
| 2008/0221554 A1 | 9/2008 | O'Connor |
| 2008/0281350 A1 | 11/2008 | Sepetka |
| 2008/0319521 A1 | 12/2008 | Norris et al. |
| 2009/0192536 A1 | 7/2009 | Berez et al. |
| 2009/0198318 A1 | 8/2009 | Berez et al. |
| 2009/0287291 A1 | 11/2009 | Becking et al. |
| 2009/0287294 A1 | 11/2009 | Rosqueta et al. |
| 2009/0299326 A1 | 12/2009 | Morsi |
| 2009/0299448 A1 | 12/2009 | Timko et al. |
| 2009/0318947 A1 | 12/2009 | Garcia et al. |
| 2010/0004671 A1 | 1/2010 | Gerberding et al. |
| 2010/0004726 A1 | 1/2010 | Hancock et al. |
| 2010/0010624 A1 | 1/2010 | Berez et al. |
| 2010/0063531 A1 | 3/2010 | Rudakov et al. |
| 2010/0069948 A1 | 3/2010 | Veznedaroglu et al. |
| 2010/0094335 A1 | 4/2010 | Gerberding et al. |
| 2010/0106240 A1 | 4/2010 | Duggal et al. |
| 2010/0152828 A1 | 6/2010 | Pakbaz et al. |
| 2010/0262124 A1 | 10/2010 | Hirszowicz et al. |
| 2010/0274276 A1 | 10/2010 | Chow et al. |
| 2010/0274346 A1 | 10/2010 | Chouinard et al. |
| 2010/0280590 A1 | 11/2010 | Sun et al. |

* cited by examiner

ANEURYSM EMBOLIZATION BY ROTATIONAL ACCUMULATION OF MASS

CROSS-REFERENCE TO RELATED APPLICATIONS

This patent application claims the priority benefits of: U.S. Provisional Patent Application No. 61/335,257 entitled "Aneurysm Embolization by Rotational Accumulation of Mass" filed on Jan. 4, 2010 by Robert A. Connor.

FEDERALLY SPONSORED RESEARCH

Not Applicable

SEQUENCE LISTING OR PROGRAM

Not Applicable

BACKGROUND

1. Field of Invention

This invention relates to treatment of aneurysms.

2. Review and Limitations of the Prior Art

An aneurysm is an abnormal localized bulging or ballooning of the wall of a blood vessel. A cerebral aneurysm is an abnormal bulging or ballooning of an intercerebral artery. The prevalence of cerebral aneurysms is in the range of 1-5%.

According to the National Institute of Neurological Disorders and Stroke (NINDS) of NIH, the incidence of reported ruptured aneurysms is about 10 per 100,000 persons per year (about 27,000 per year in the U.S.). Approximately one third to one half of people who suffer a ruptured cerebral aneurysm die within one month and, among those who survive, approximately one half suffer significant deterioration of brain function. The vast majority of cerebral aneurysms form in the junction of arteries known as the Circle of Willis where arteries come together and from which these arteries send branches to different areas of the brain.

The most common methods of treating aneurysms are surgical clipping (placing a clamp on the aneurysm from outside the vessel) and endovascular coiling (inserting flexible coils into the aneurysm from inside the vessel). During the past three decades, there has been a general trend away from surgical clipping and toward less-invasive endovascular methods of treating aneurysms such as coiling. The limitations of surgical clipping include the risks of invasive surgery and difficulty accessing aneurysms in some areas. We will now discuss endovascular coiling in greater depth because the invention disclosed here is more similar to coiling than to clipping. The following are four serious problems with endovascular coiling in the prior art that will be corrected by the present invention:

1. Limited Fill Volume Due to Resilient and Springy Coils

Endovascular coils in the prior art tend to be relatively resilient and springy. They are often metal. These qualities are needed in traditional coiling in order to create the surface tension between the coils and the aneurysm walls that holds the coils within the aneurysm sack. The coil loops do not form a solid mass within the aneurysm and would likely prolapse into the parent vessel if they were not resilient and springy. However, the resilient and springy nature of coils in the prior art limits the percentage of the aneurysm volume that can be filled by these coils. As these coils overlap in loops, there are often large gaps between them. Fill rates for the aneurysm sack volume can be as low as 25%-50%. Much of the volume of the aneurysm remains unfilled. As a result of these low fill rates, sometimes blood can continue to flow into the aneurysm and the aneurysm can continue to expand or even rupture.

2. Limited Fill Volume Due to Radially Inward Filling Process

In deployment of the endovascular coils in the prior art, accumulation of coil mass starts around the perimeter of the aneurysm. Accumulation of mass then moves radially-inward toward the center of the aneurysm sack with successive coil loops. Unfortunately, coil maneuverability can become quite constricted as the remaining central volume shrinks. Visibility can also be difficult inside the hollow ball of perimeter coils. Accordingly, it can be difficult to achieve a high percentage of fill volume inside the mass of coils and for the aneurysm overall. As a result, the mass of coils can be relatively hollow and the coils can compact over time. This can allow recanalization of the aneurysm, continued aneurysm expansion, and even aneurysm rupture.

3. Coil Prolapse Due to Randomness of Coil Loop Directions

In deployment of endovascular coils in the prior art, the directionality of looping within the aneurysm during coiling is constantly changing, highly variable, and somewhat random in nature. Although a talented and experienced practitioner can exert some control over the changing directionality of coil looping by manipulating the device from outside the patient's body, it can be laborious for the practitioner to constantly work at avoiding having the loops turn in a direction that could prolapse into the parent vessel. Coil loops that prolapse into the parent vessel can block blood flow in real time. Prolapsed coils can also cause embolization or stoke in the future.

4. Long Procedure Time Due to Randomness of Coil Loop Directions

In addition to the possibility of coil prolapse into the parent vessel due to the randomness of changing loop directionality in traditional endovascular coiling, this randomness also makes the procedure time consuming. It can be very time-consuming for a practitioner to gradually snake coils around the aneurysm, one loop at a time, in different directions. This is especially true when multiple coils are used or when coils with different characteristics are used at different stages in the procedure.

For these four reasons, despite significant progress in surgical clipping and endovascular coiling during the past two decades, there remains a significant unmet clinical need for development of a new option to treat cerebral aneurysms that can address these four problems. The invention that we will now disclose is a novel option for treating cerebral aneurysms that can address these four problems and meet this unmet clinical need.

SUMMARY AND ADVANTAGES OF THIS INVENTION

This invention is a device for reducing blood flow into an aneurysm in order to promote therapeutic embolization of the aneurysm. The device comprises: at least one core member that is inserted into an aneurysm; and at least one longitudinal flexible member that is wound repeatedly around the core member within the aneurysm. The longitudinal flexible member is wound around the core member until the rotational accumulation of the flexible member reduces blood flow into the aneurysm and promotes therapeutic embolization of the aneurysm. This invention corrects the four problems with coils in the prior art that were just discussed in the previous section, as follows:

1. Corrects Limited Fill Volume Due to Resilient and Springy Coils

Rotational accumulation of mass around a core member, as disclosed in this present invention, corrects this problem. With rotational accumulation of mass around a core member, the longitudinal flexible members do not have to be resilient and springy. They can be held within the aneurysm sack due to self-adhesion in a manner that is not possible with traditional coils and can be densely packed into a solid mass within the aneurysm. The longitudinal flexible members that are wound around the core member may be filaments or strings. This can enable filling a much higher volume of the aneurysm, which can reduce the chances that the aneurysm will continue to expand or rupture.

2. Corrects Limited Fill Volume Due to Radially Inward Filling Process

Rotational accumulation of mass around a core member, as disclosed in this present invention, corrects this problem. In this invention, accumulation of mass starts at the center and then moves radially-outward. Especially with a longitudinal flexible member winding around the core member, this present invention does not constrict movement and also allows much denser packing volumes throughout the entire radial range of the aneurysm. It can also improve visibility during the procedure because loop accumulation is not obscured by already-accumulated loops.

3. Corrects Coil Prolapse Due to Randomness of Coil Loop Directions

Rotational accumulation of mass around a core member, as disclosed in this present invention, corrects this problem. In this invention, the directionality of looping is primarily constrained to a single plane. Generally this plane of rotational looping is parallel with the neck of the aneurysm. In contrast to current coiling methods, this avoids coils that can loop in planes that are perpendicular to the neck of the aneurysm. In this manner, this invention avoids loops that are perpendicular to the neck of the aneurysm that can easily prolapse into the parent vessel.

4. Corrects Long Procedure Time Due to Randomness of Coil Loop Directions

Rotational accumulation of mass around a core member, as disclosed in this present invention, corrects this problem. The simple rotational process can quickly and efficiently fill the entire radial space of an aneurysm with accumulated mass. There is no need to manage partially-random changes in loop direction to avoid coils prolapsing into the parent vessel. Ideally, the practitioner will be able to just: insert this device into the aneurysm; activate the rotational accumulation of mass until the aneurysm is appropriately filled (either based on imaging or automatic shut off); and then detach and withdraw the catheter. In this manner, this invention can reduce operating time, thereby reducing risk and expense for the patent and the health care system.

INTRODUCTION TO THE FIGURES

These figures show different examples of how this invention may be embodied, but do not limit the full generalizability of the claims.

FIGS. 1-5 show a first example, in three stages of deployment, featuring a spool (functioning as the core member) and a flexible filament (functioning as the longitudinal flexible member).

FIGS. 1 and 2 show this example in the first stage of deployment, before the spool has been rotated. FIG. 1 shows this in a semi-transparent perspective. FIG. 2 shows this in an opaque perspective.

FIGS. 3 and 4 show this example in the second stage of deployment, after the spool has been rotated, but before the catheter has been removed. FIG. 3 shows this in a semi-transparent perspective. FIG. 4 shows this in an opaque perspective.

FIGS. 6-9 show a second example of this invention, in four stages of deployment, featuring a spool (as the core member), two flexible filaments (as longitudinal flexible members), and an inflatable guide loop (as a guide for the filaments as they wind around the spool).

FIGS. 10-13 show a third example of this invention, in two stages of deployment, wherein the axis of the rotating spool is parallel to the plane of the aneurysm neck opening.

FIGS. 14-23 show a fourth example, in five stages of deployment, in which there are multiple overlapping filament disks. FIGS. 14-18 show this example from a semi-transparent perspective. FIGS. 19-23 show this same example from an opaque perspective.

FIGS. 24-29 show a fifth example of the invention, during six stages of deployment. In this example, a filament is wound around a axially-rotating ("twisting") loop instead of a rotating spool, creating an embolic member that looks like a "ball of yarn."

FIGS. 30 and 31 show an example that is similar to the example that was originally shown in FIGS. 1 through 5, except that now the device is delivered by a single catheter.

FIGS. 32-34 show an example, with three stages of deployment, that is similar to the example that was originally shown in FIGS. 1 through 5, except that now the guide arm is detached from the catheter and left behind in the aneurysm when the catheter is removed from the body.

DETAILED DESCRIPTION OF THE FIGURES

These figures show different examples of how this invention may be embodied. However, these examples are not exhaustive and these figures do not limit the full generalizability of the claims.

FIGS. 1-5 show a first example of this invention, in three stages of deployment, to occlude an aneurysm. This first example of the invention includes: a spool 102, functioning as the core member, that is inserted into aneurysm 101 and then rotated around an axis that is perpendicular to the plane of the aneurysm neck opening; flexible filament 105, functioning as the longitudinal flexible member, that is attached to spool 102 and winds around spool 102 as the spool rotates; pivoting guide arm 106 that guides filament 105 as it winds around spool 102; and a catheter with lumens 104 and 109 that is used to insert the spool, flexible filament, and guide arm into the aneurysm. Guide arm 106 is connected to the end of catheter lumen 109 by means of pin 201, thereby allowing guide arm 106 to pivot on the end of catheter lumen 109. Spool 102 is attached to, and rotated by, rotating wire 103.

In this example, spool 102, guide arm 106, and catheter lumens 104 and 109 are made from material selected from the group consisting of ethylene propylene diene monomer, latex, silicone, polyvinyl chloride, and polyurethane. In this example, filament 105 is made from material selected from the group consisting of nylon, polyester, polyethylene, polypropylene, polytetrafluorethylene, polytetrafluoroethene, acetate, acrylic, cotton, linen, rayon, silk, and spandex. In this example, filament 105 is slightly sticky so that it adheres to itself and does not unravel once wound around spool 102. In a variation on this example, filament 105 may be covered with microscale hook-and-loop fibers that cause it to adhere to itself when wound around spool 102.

Figure 1:
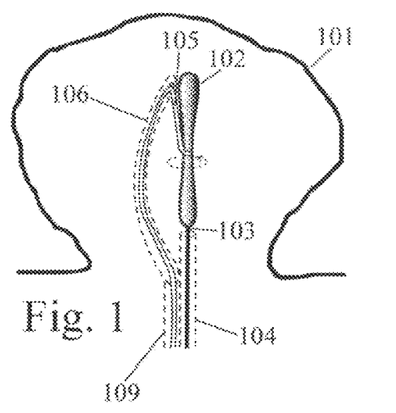
Figure 2:
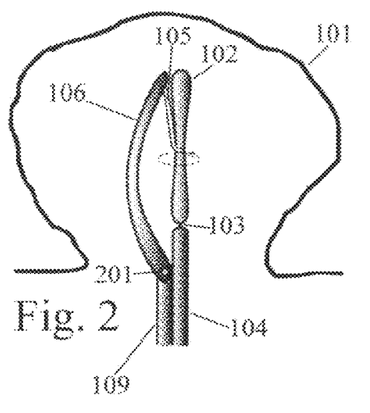

FIGS. 1 and 2 show this first example of the invention in the first stage of deployment. In this first stage, spool 102, filament 105, and guide arm 106 have been inserted into aneurysm 101, but spool 102 has not yet been rotated. FIG. 1 shows guide arm 106, catheter lumen 104, and catheter lumen 109 in a transparent manner so that one can see: how filament 105 travels through the center of catheter lumen 109, through the center of guide arm 106, out of a hole in the end of guide arm 106 and then connects to spool 102; and how rotating wire 103 travels through the center of catheter lumen 104 to drive the rotation of spool 102. FIG. 2 shows the same configuration as FIG. 1, but with all parts shown as opaque to provide a good overall three-dimensional view of the device.

Figure 3:
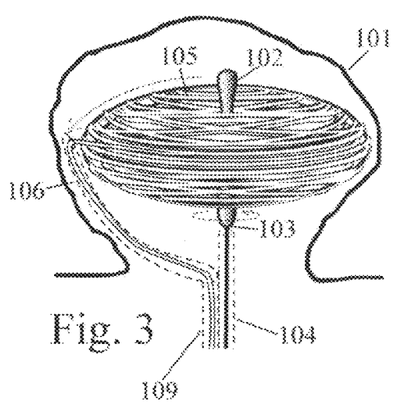
Figure 4:
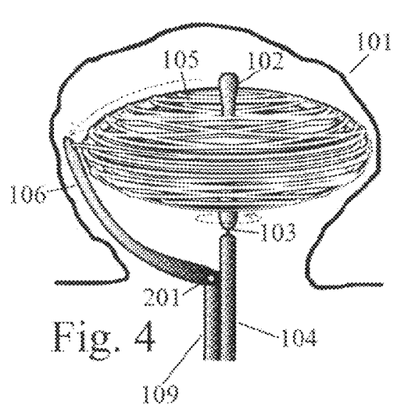

FIGS. 3 and 4 show this first example of the invention in the second stage of deployment. In this second stage: spool 102 has been rotated repeatedly, winding filament 105 around spool 102 in order to form a filament disk that largely fills the width of the aneurysm; and guide arm 106 has pivoted outwards as winding filament 105 has accumulated around spool 102. There are many examples in the prior art of ways to rotate wires inside catheters and the exact method of rotation is not central to this invention, so the exact method of wire rotation is not specified herein. In alternative examples, at least one longitudinal flexible member (a filament in this example) may be wound repeatedly around at least one core member (a spool in this example) by one or more rotations selected from the group consisting of: rotation of the at least one core member; and rotation of the longitudinal flexible member around the core member.

FIG. 3 shows this second stage of deployment with guide arm 106, catheter lumen 104, and catheter lumen 109 shown as transparent. FIG. 4 shows the same configuration as FIG. 3, but with all parts shown as opaque to provide a good overall three-dimensional view of the device.

In this example, there is one longitudinal flexible member, filament 105, which is wound around one core member, spool 102. In other examples, there may be more than one core member, more than one longitudinal flexible member, or more than one of each. In this example, one longitudinal flexible member is wound repeatedly around one core member by rotation of the core member. In another example, multiple longitudinal flexible members may be wound repeatedly around one or more core members by rotation of the longitudinal flexible members around the core members. In various examples, variation in the number, thickness, configuration of multiple longitudinal flexible members may be used to more accurately fill aneurysms of different shapes and sizes.

In this example, the longitudinal flexible member is filament 105. In various other examples, at least one longitudinal flexible member may be selected from the group consisting of: biocompatible thread, biocompatible string, biocompatible filament, biocompatible tape, biocompatible wire, biocompatible coil, and string of connected biocompatible members.

Figure 5:
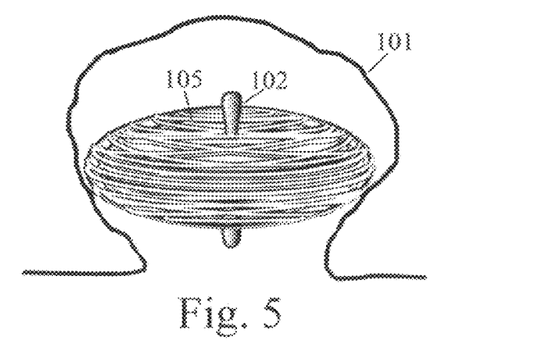
FIG. 5 shows this example in the third stage of deployment, after the catheter has been detached and removed from the body. The accumulated mass of filament that has been wound around the spool is left behind in the aneurysm to reduce blood flow into the aneurysm and thereby promote therapeutic embolization of the aneurysm.

FIG. 5 shows this first example of this invention in the final stage of deployment. In FIG. 5, guide arm 106, rotating wire 103, and catheter lumens 104 and 109 have been detached and removed from the filament 105 disk and spool 102. This leaves filament 105 disk behind in the aneurysm to occlude the aneurysm neck, reduce blood flow into the aneurysm, and promote therapeutic embolization of the aneurysm. With the neck of the aneurysm occluded by the disk formed by winding filament 105 around spool 102, blood flow to the aneurysm is greatly reduced and therapeutic embolization of the aneurysm begins.

In this example, filament 105 is pre-cut to a length that creates the proper size filament disk, so that guide arm 106 automatically detaches from the filament disk when the cut end of filament 105 slips out of the hole in the guide arm. In a variation on this example, there may be a cutting mechanism within guide arm 106 to cut filament 105 that is remotely activated from the end of catheter 109 outside the patient's body. This cutting can cause guide arm 106 to detach from the filament disk.

In this example, rotating wire 103 is detached from spool 102 by application of a small electric current through the wire that melts the wire at the place where it links to spool 102. In a variation on this example, rotating wire 103 may be detached from spool 102 by withdrawal of a linchpin operated from a remote location outside the patient's body. In various examples, members of the device that are to remain in the aneurysm may be detached from the members of the device to be withdrawn from the body by means selected from the group consisting of: electricity; laser; ultrasound; and mechanical mechanism.

In this example, the core member is spool 102. In various other examples, the core member may have a shape selected from the group consisting of: cylinder with rounded ends, figure-eight, hour glass, torus, ellipse, oval, sphere, cube, and fork with rounded prongs. In various examples, one or more core members and one or more longitudinal flexible members may be: delivered to the aneurysm by a catheter; detached from the catheter by electricity, ultrasound, laser, or mechanical means; and then left within the aneurysm after the at least one longitudinal flexible member has been wound repeatedly around the at least one core member.

In this example, the guiding structure is a guide arm 106 that is removed when the catheter is removed. In various examples, the guiding structure may be a selected from one or more structures in the group consisting of: an arm, a wire, a cable, a catheter, a rod, a loop, a balloon, a structure with shape memory. In this example, the guiding structure is: delivered to the aneurysm by a catheter; and then withdrawn from the body after the longitudinal flexible member has been wound repeatedly around the at least one core member. In other examples, the guiding structure may be: delivered to the aneurysm by a catheter; detached from the catheter by electricity, ultrasound, laser, or mechanical means; and then left within the aneurysm after the at least one longitudinal flexible member has been wound repeatedly around the at least one core member. The later may allow a larger mass of the longitudinal flexible member to accumulate and remain in the aneurysm, without harming the aneurysm wall when trying to remove the guide structure from the aneurysm.

FIGS. 6-9 show a second example of this invention. These figures show this second example in four stages of deployment within an aneurysm. This second example of the invention includes: spool 601 (functioning as a core member) that is inserted into, and rotated within, aneurysm 101 around an axis that is perpendicular to the plane of the aneurysm neck opening; two flexible filaments 604 and 605 (serving as multiple longitudinal flexible members) that are attached to, and wound around, opposite sides of spool 601 as the spool rotates; inflatable guide loop 606 (serving as a guide structure), with small sub-loops 607 and 608 centrally attached, that encircles spool 601 and guides filaments 604 and 605 as they wind around spool 601; and catheter 609. Catheter 609, in turn, contains: channels for filaments 604 and 605 to travel into the aneurysm, channels for pressurized air (or liquid) to inflate guide loop 606; and catheter 603 to contain rotating wire 602 that rotates spool 601. Catheter 609 is shown as transparent so that one can see how filaments 604 and 605 and catheter 603 travel through it. In this example, filaments 604 and 605 are threaded through small sub-loops 607 and 608 that are centrally attached to inflatable guide loop 606 in order to keep these filaments from getting tangled and to evenly guide them as they wind around rotating spool 601. In this example, spool 601 is attached to rotating wire 602 that travels through catheter 603.

In this example, spool 601, catheter 609, catheter 603, and small sub-loops 607 and 608 are made from material selected from the group consisting of ethylene propylene diene monomer, latex, silicone, polyvinyl chloride, and polyurethane. In this example, filaments 604 and 605 are made of material selected from the group consisting of nylon, polyester, polyethylene, polypropylene, polytetrafluorethylene, polytetrafluoroethene, acetate, acrylic, cotton, linen, rayon, silk, and spandex. In this example, inflatable guide loop 606 is made from material selected from the group consisting of ethylene propylene diene monomer, latex, silicone, polyvinyl chloride, and polyurethane. In this example, filaments 604 and 605 are slightly sticky so that they adhere to themselves and to each other and do not unravel once wound around spool 601. In a variation on this example, these filaments may be covered with microscale hook-and-loop fibers that cause them to adhere to themselves and to each other and do not unravel once wound around spool 601.

Figure 6:
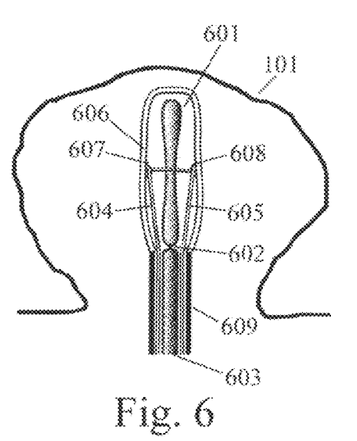
FIG. 6 shows this example in the first stage of deployment, before the guide loop has been inflated and before the spool has been rotated.
Figure 7:
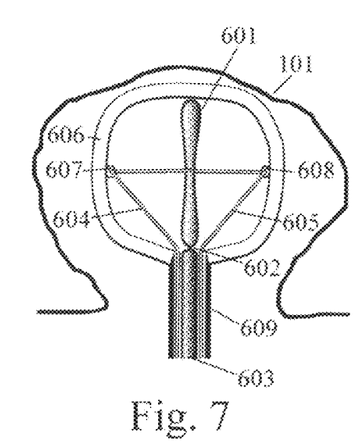
FIG. 7 shows this example in the second stage, after the guide loop has been inflated, but before the spool has been rotated.

FIG. 6 shows this second example of the invention in the first stage of deployment. In this first stage, spool 601, filaments 604 and 605, and inflatable guide loop 606 have been inserted into aneurysm 101, but guide loop 606 has not yet been inflated and spool 601 has not yet been rotated. FIG. 7 shows this example in a second stage of deployment. In this second stage, spool 601, filaments 604 and 605, and inflatable guide loop 606 have been inserted into aneurysm 101 and guide loop 606 has been inflated, but spool 601 has not yet been rotated.

Figure 8:
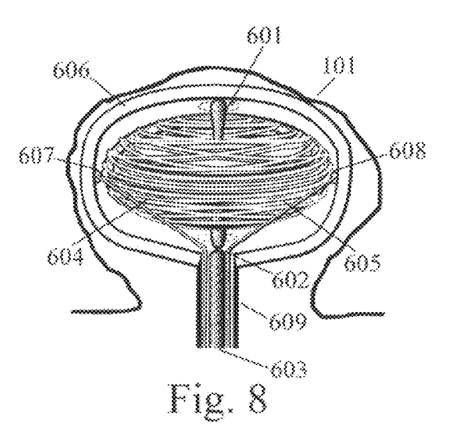
FIG. 8 shows this example in the third stage, after the guide loop has been inflated and the spool has been rotated, but before the catheter has been withdrawn.

FIG. 8 shows this second example of the invention in the third stage of deployment. In this third stage, spool 601, filaments 604 and 605, and inflatable guide loop 606 have been inserted into aneurysm 101, guide loop 606 has been inflated, and spool 601 has been rotated repeatedly to wind filaments 604 and 605 into a filament disk around spool 601. There are many ways in the prior art to rotate wires inside catheters and the exact method is not central to this invention, so the exact method of wire rotation is not specified herein. One advantage of this second example of the invention shown in FIGS. 6-9, as compared to the first example of this invention shown in FIGS. 1-5, is that the inflatable loop guide in the second example protects the aneurysm walls from contact with the spinning spool and filament disk.

Figure 9:
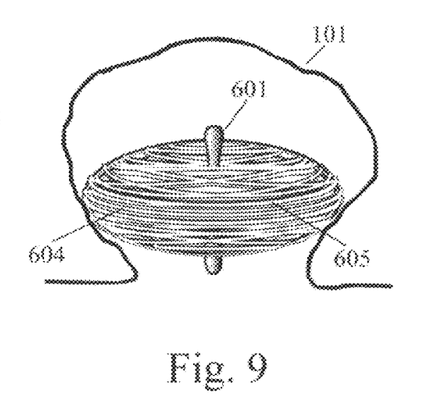
FIG. 9 shows this example in the fourth stage, after catheter has been withdrawn.

FIG. 9 shows this second example of the invention in the final stage of deployment. In this final stage, guide loop 606, rotating wire 602, and catheter 609 have been detached and removed. This leaves behind in the aneurysm a disk of wound filaments 604 and 605 to occlude the aneurysm, reduce blood flow to the aneurysm, and promote therapeutic embolization of the aneurysm. In this example, the guide loop 606 is detached from the disk of wound filaments when the ends of filaments 604 and 605 slip through small sub-loops 607 and 608. In this example, rotating wire 602 is detached from spool 601 when application of a small electric current melts the wire at its connection with the spool. Other variations on this example may have other means of detaching guide loop 606 from the filament disk and detaching rotating wire 602 from the spool. In various examples, at least one longitudinal flexible member: may pass through at least one guiding structure to guide the longitudinal flexible member as it winds repeatedly around the core member; and the at least one guiding structure is selected from one or more of the group consisting of: an arm, a loop, a balloon, a wire, a catheter, and a structure made from memory material.

FIGS. 10-13 show a third example of this invention. In this example, the axis of the rotating spool 1001 is parallel to the plane of the aneurysm neck opening. One advantage of having a spool with a rotational axis that is parallel to the plane of the aneurysm neck opening is that no guide arm or guide loop is required.

Figure 10:
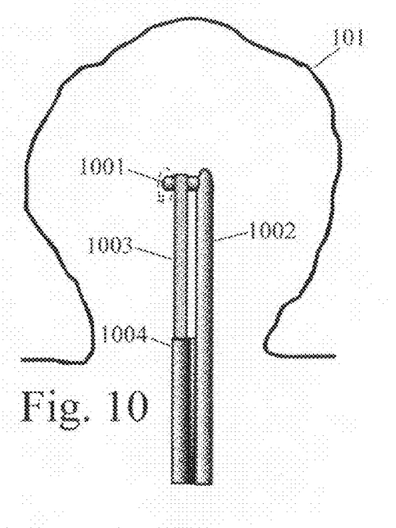
FIGS. 10 and 11 show side and frontal perspectives of this example in the first stage, before spool rotation.
Figure 11:
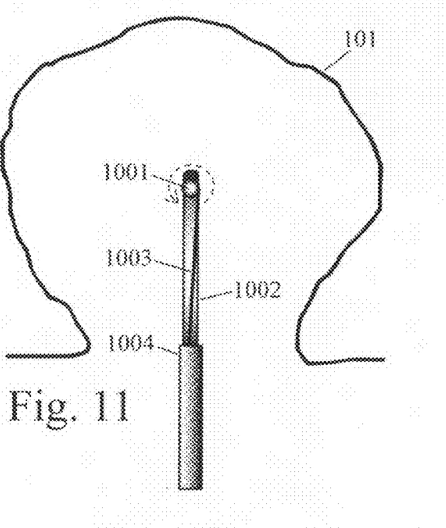
Figure 12:
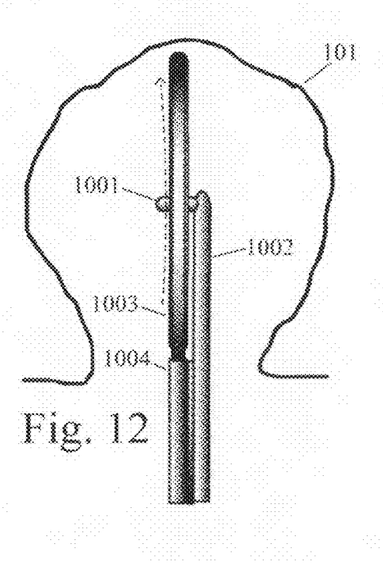
FIGS. 12 and 13 show side and frontal perspectives of this example in the second stage, after spool rotation.
Figure 13:
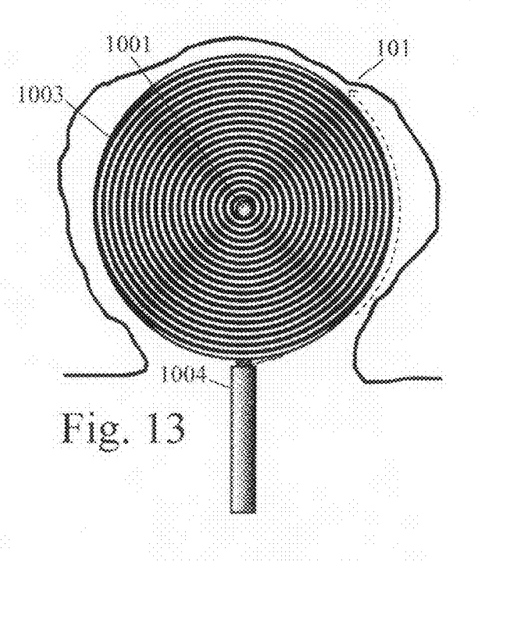

FIGS. 10-13 show this third example in two stages of deployment within an aneurysm. The first stage is after insertion, but before spool rotation. The second stage is after both insertion and spool rotation. FIG. 10 shows the first stage from a side perspective on spool 1001. FIG. 11 shows the first stage from a frontal perspective on spool 1001. FIG. 12 shows the second stage from a side perspective on spool 1001. FIG. 13 shows the second stage from a frontal perspective on spool 1001. This third example of the invention includes: spool 1001 that is inserted into, and rotated within, aneurysm 101 around an axis that is parallel to the plane of the aneurysm neck; tape-like filament 1003 that is attached to, and wound around, spool 1001 as the spool rotates; catheter 1004 that provides a channel for filament 1003; and catheter 1002 that provides support and rotational drive for spool 1001.

FIG. 10 shows the first stage, before rotation of spool 1001, from a side perspective on spool 1001. Spool 1001 is supported in perpendicular extension from catheter 1002. Tape-like filament 1003 extends out from a channel in catheter 1004 to connect with spool 1001. In FIG. 10, the device has been inserted into the neck of aneurysm 101. FIG. 11 shows the same configuration as shown in FIG. 10, but from a frontal perspective on spool 1001. FIG. 12 shows the second stage, after repeated rotation of spool 1001, from a side perspective on spool 1001. In FIG. 12, tape-like filament has been wound around spool 1001, forming a filament disk. FIG. 13 shows this same configuration from a frontal perspective on spool 1001, wherein the filament disk connected to catheter 1004 suggests a "lollypop" shape. In FIG. 13, catheter 1002 is obscured behind 1004. In a final deployment stage after FIG. 13, the filament 1003 disk is detached from the catheters and remains behind to occlude the aneurysm. Such detachment can be achieved by melting the connection between spool 1001 and catheter 1002 with a small electric current. The end of catheter 1004 serves to guide filament 1003 as it winds around rotating spool 1001. In various examples, at least one longitudinal flexible member may wind around a core member with a rotational axis with an orientation that is selected from the group consisting of: substantially perpendicular to the plane of the aneurysm neck; and substantially parallel to the plane of the aneurysm neck.

Figure 14:
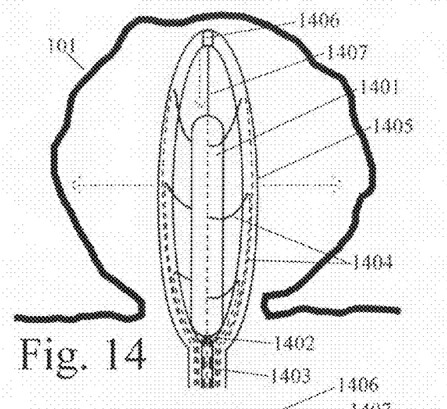
FIG. 14 shows stage one of deployment, immediately after insertion into the aneurysm.
Figure 15:
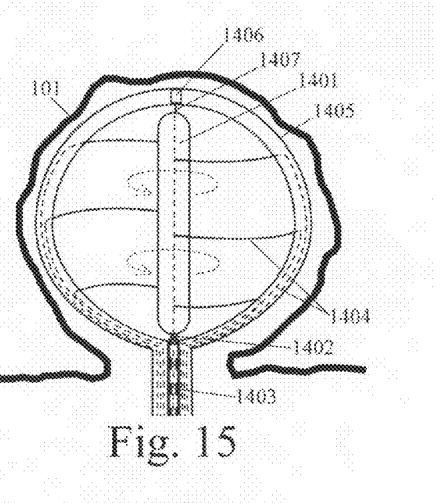
FIG. 15 shows stage two, after contraction of a guide loop into a circular shape.
Figure 16:
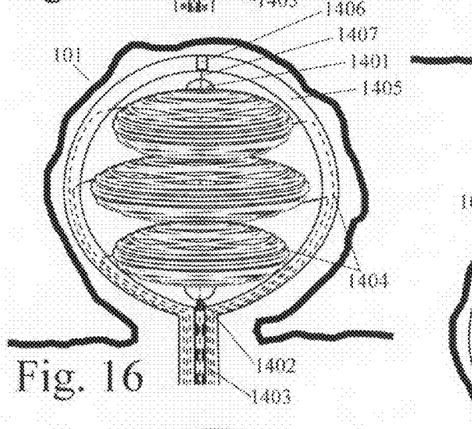
FIG. 16 shows stage three, after rotation of the spool.
Figure 17:
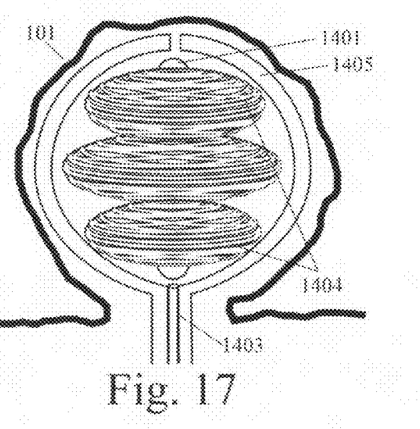
FIG. 17 shows stage four, after detachment of the six filaments and the spool.
Figure 18:
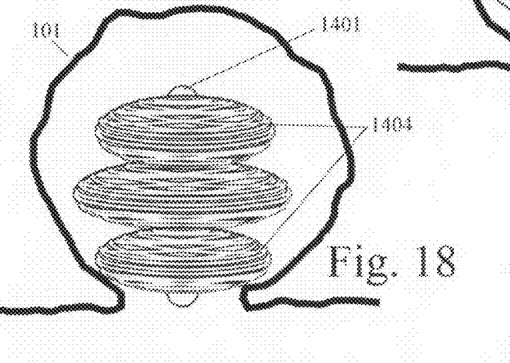
FIG. 18 shows stage five, after removal of the catheter from the aneurysm.
Figures 19, 20, 21, 22, 23:
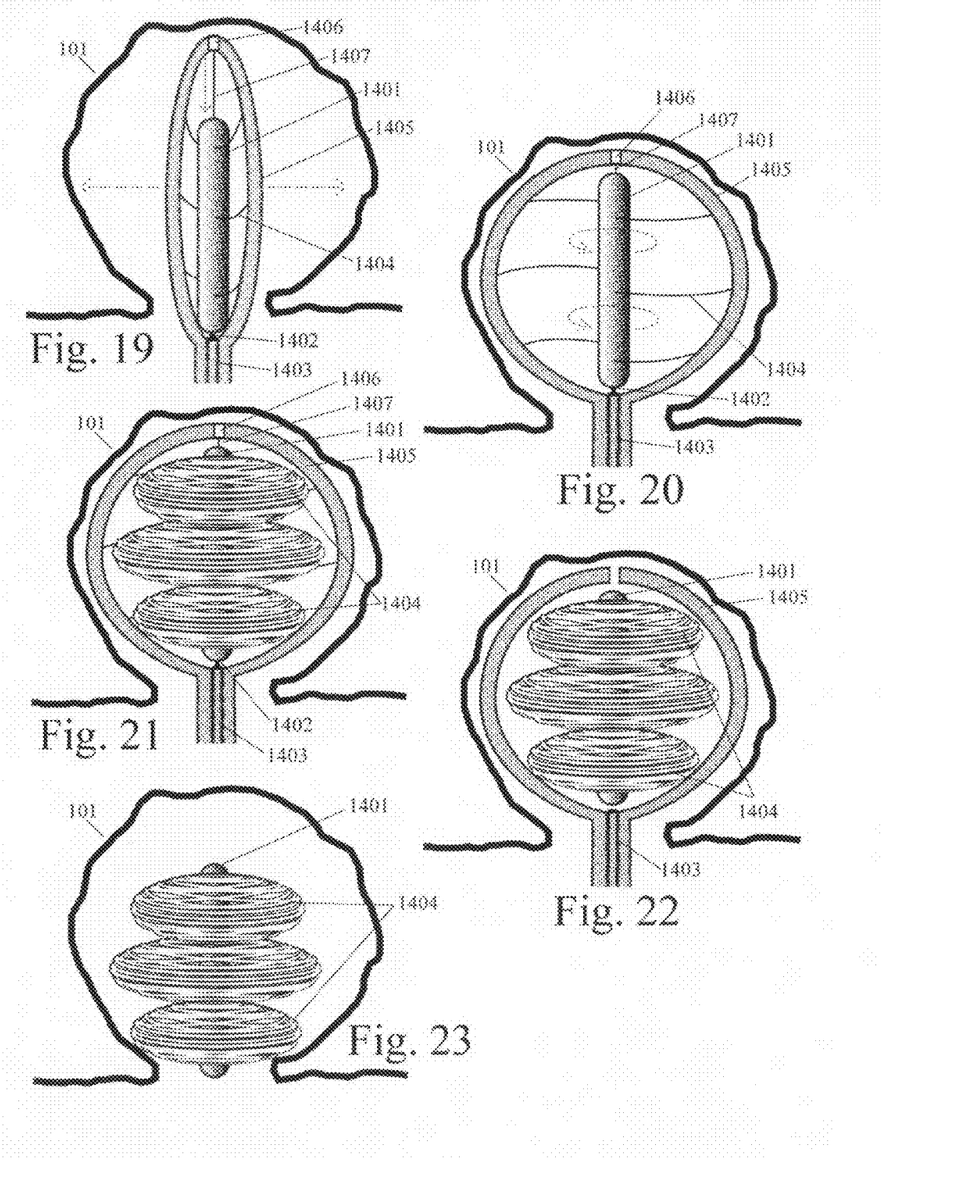
FIGS. 19-23 show these same five stages, but with an opaque perspective.

FIGS. 14-18 show a fourth example of this invention, one in which multiple overlapping filament disks are formed in order to occlude an aneurysm. These figures show deployment of this example in five stages. We first provide an introduction to these figures to highlight the five stages of deployment, followed by discussion of these figures in greater detail. FIG. 14 shows the device in stage one, immediately after insertion of the device into the aneurysm. FIG. 15 shows the device in stage two, after contraction of a guide loop from an oval shape into a circular shape. FIG. 16 shows the device in stage three, after repeated rotation of the spool that winds six filaments around the spool. FIG. 17 shows the device in stage four, after detachment of the six filaments and the spool from the rest of the device. FIG. 18 shows the device in the fifth and final stage, after removal of the rest of the device from the aneurysm. This leaves behind within the aneurysm an embolic member comprising three overlapping filament disks. In FIGS. 14-18, device components other than the filaments are shown as transparent in order to show how the filaments and other components are located within the guide loop and catheter.

We now discuss FIGS. 14-18 in greater detail. FIG. 14 shows this fourth example of the invention including: spool 1401 that rotates on an axis perpendicular to the plane of the aneurysm neck; six filaments 1404 connected to spool 1401, with three filaments evenly spaced on each of the opposite sides of the spool; guide loop 1405 that is held by sliding wire 1407 in an oval configuration for easy insertion into the aneurysm; rotating flexible column 1402 that is connected to, and rotates, spool 1401; and catheter 1403 that provides a protected channel for rotating flexible column 1402. In FIG. 14, the device has just been inserted into aneurysm 101. FIG. 15 shows this device in the second stage of deployment. In FIG. 15, after the device has been inserted into aneurysm 101, sliding wire 1407 is pulled toward the end of catheter 1403 in order to contract guide loop 1405 within the aneurysm from an oval shape (for easy insertion) to a circular shape (for filament guiding).

FIG. 16 shows this fourth example of the invention in a third stage of deployment. In FIG. 16, after the device has been inserted into the aneurysm and guide loop 1405 has been contracted into a circular shape, spool 1401 is repeatedly rotated by rotation of flexible column 1402. There are many different ways to rotate a flexible wire or flexible column in the prior art and the exact rotational mechanism is not central to this invention, so the exact method is not specified here. In this example, there are six filaments 1404 threaded through holes in guide loop 1405 that wind around spool 1401 as the spool rotates There are three filaments connected with the spool in an evenly-spaced manner on each of the opposite sides of the spool. As the spool rotates, the accumulating winding filaments 1404 form three overlapping filament disks around a common axis. Creating an embolic member comprising multiple overlapping disks can occlude aneurysms with relatively-spherical shapes better than an embolic member comprising a single disk.

FIG. 17 shows this example of the invention in a fourth stage of deployment. In FIG. 17, after filaments 1404 have been wound around the spool 1401 to create three embolic disks of the desired size, filaments 1404 are detached from guide loop 1405, the center section of guide loop 1406 is melted by administration of a small electric current, and rotating flexible column 1402 is detached from spool 1401. This allows removal of the guide loop and catheter, leaving the filament disks and spool behind to occlude the aneurysm, reduce blood flow, and promote therapeutic embolization of the aneurysm. FIG. 18 shows the device after removal of the guide loop and catheter has occurred.

FIGS. 19-23 show the same example that was shown in FIGS. 14-18, in the same five stages of deployment, except that all components of the device are shown as opaque in order to provide a good overall three-dimensional perspective of the device.

FIGS. 24-29 show a fifth example of the invention during six stages of deployment. In this example, a filament is wound around a axially-rotating ("twisting") loop instead of a rotating spool, creating an embolic member that looks like a "ball of yarn." The "ball of yarn" embolic member created in this example can be more spherical in shape than the filament disks created in prior examples, which can be advantageous for certain shape aneurysms.

Figure 24:
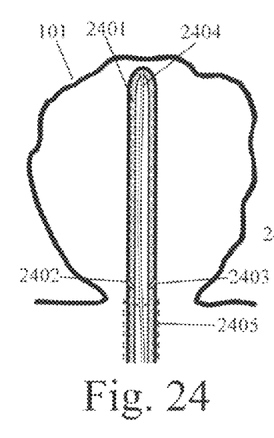
FIG. 24 shows the first stage, wherein a resilient loop extends distally outward from a catheter as it is inserted into an aneurysm.

FIG. 24 shows this example during the first stage of deployment, wherein resilient loop 2401 extends distally outward from catheter 2405 as it is inserted into aneurysm 101. During this insertion, resilient loop 2401 is in a distally-extended configuration with an oval-point distal end. FIG. 24 also shows two separately-meltable sections, 2402 and 2403, of resilient loop 2401 that are close to where the two sides of loop 2401 extend out from the interior of catheter 2405. FIG. 24 also shows flexible filament 2404 extending out from the center of catheter 2405 and connecting with resilient loop 2401 at the loop's most distal location.

Figure 25:
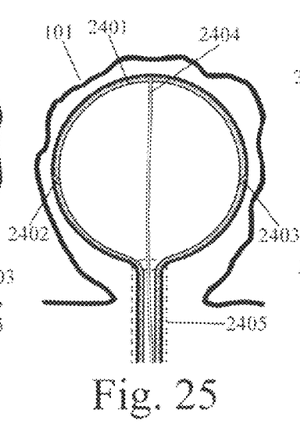
FIG. 25 shows the second stage, wherein an additional length of the resilient loop is pushed outward from the interior of catheter to change the loop into a circular shape.

FIG. 25 shows this example during the second stage of deployment, wherein additional length of resilient loop 2401 is pushed outward from the interior of catheter 2405. The combination of additional loop length being pushed out from catheter 2405 and the inward tension from flexible filament 2404 on the loop's most distal location causes loop 2401 to change from a generally-elongated shape into a generally-circular shape.

Figure 26:
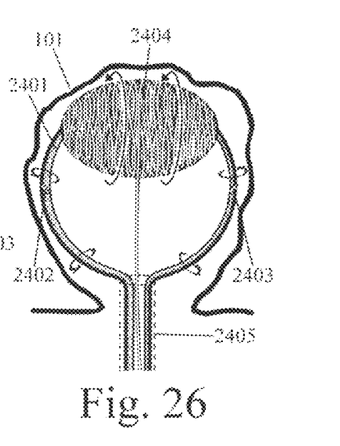
FIG. 26 shows the third stage, wherein the loop is rotated ("twisted") around its internal axis, causing a filament to wind around loop. The accumulating winding filament creates an embolic member within the aneurysm that is similar in appearance to a "ball of yarn."
Figure 27:
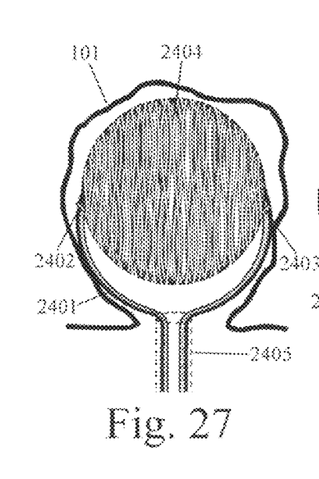
FIG. 27 shows the fourth stage, wherein the "ball of yarn" embolic member has grown to the desired size and the rotating motion stops.

FIG. 26 shows this example during the third stage of deployment, wherein the tubular structure comprising loop 2401 is rotated ("twisted") around its internal axis. In this example, this rotation originates from outside the patient's body and is conveyed through catheter 2405 to loop 2401 within the aneurysm. The rotation of the loop causes filament 2404 to wind around loop 2401 within the aneurysm. The accumulating winding filament creates an embolic member within the aneurysm that is similar in appearance to a "ball of yarn." FIG. 27 shows the fourth stage of deployment, wherein the "ball of yarn" embolic member has grown to the desired size and the rotating motion stops.

Figure 28:
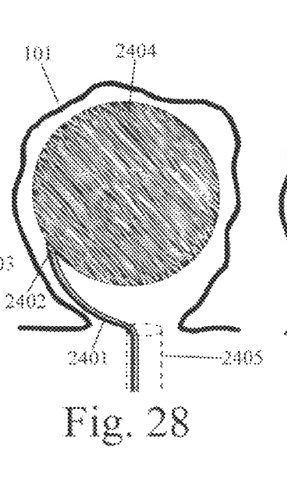
FIG. 28 shows the fifth stage, wherein one section of the loop has been melted to detach one side of the "ball of yarn" embolic member.
Figure 29:
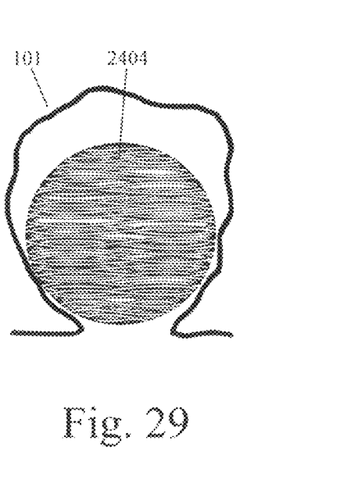
FIG. 29 shows the sixth stage, wherein another section of the loop has been melted to completely detach the "ball of yarn" embolizing member and the catheter has been withdrawn.

FIG. 28 shows the fifth stage of deployment, wherein one of the two separately-meltable sections of the loop, section 2403, has been melted by a small electric current sent through the loop. This detaches one side of the "ball of yarn" embolic member. FIG. 29 shows the sixth stage of deployment, wherein the second of the two separately-meltable sections of the loop, section 2402, has been melted by a small electric current sent through the loop. This completely detaches the "ball of yarn" embolic member within the aneurysm. The embolic member occludes the aneurysm, reduces blood flow through the aneurysm, and promotes therapeutic embolization of the aneurysm.

Figure 30:
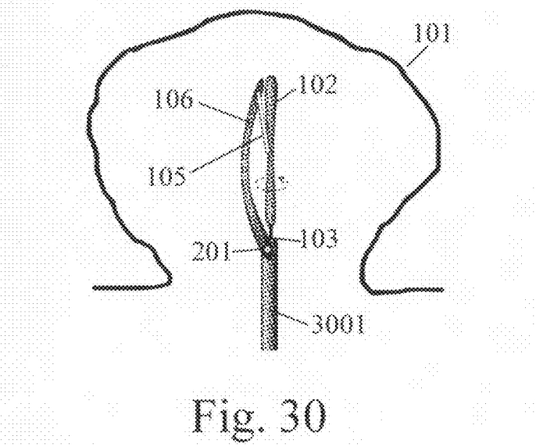
FIG. 30 shows the first stage, before the spool has been rotated.
Figure 31:
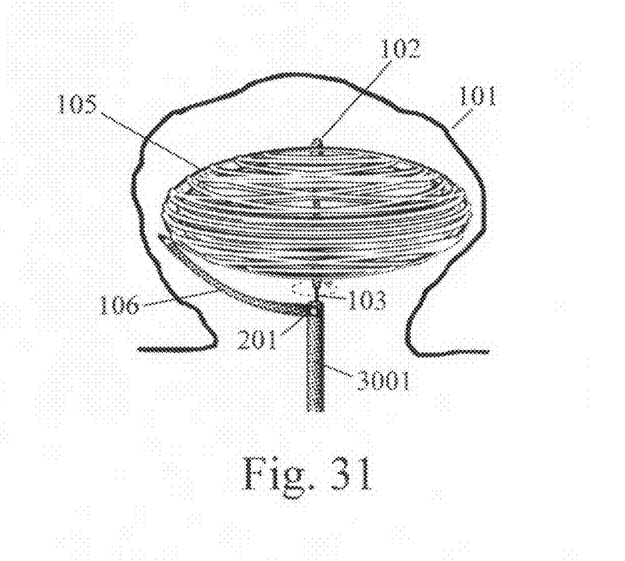
FIG. 31 shows the second stage, after the spool has been rotated.

FIGS. 30 and 31 show another example of the invention. This example is similar to the example that was originally shown in FIGS. 1 through 5, except that now guide arm 106, filament 105, and rotating wire 103 are delivered into the aneurysm by means of a single catheter 3001 instead of by means of two catheters. Use of a single catheter may make it easier to navigate the device through narrow and twisting blood vessels. FIG. 30 shows this example in the first stage of deployment wherein spool 102, filament 105, and guide arm 106 have been inserted into aneurysm 101, but spool 102 has not yet been rotated. FIG. 31 shows this example in the second stage of deployment wherein spool 102 has been rotated repeatedly, winding filament 105 around spool 102 in order to form a filament disk that largely fills the width of the aneurysm; and guide arm 106 has pivoted outwards as winding filament 105 has accumulated around spool 102.

Figure 32:
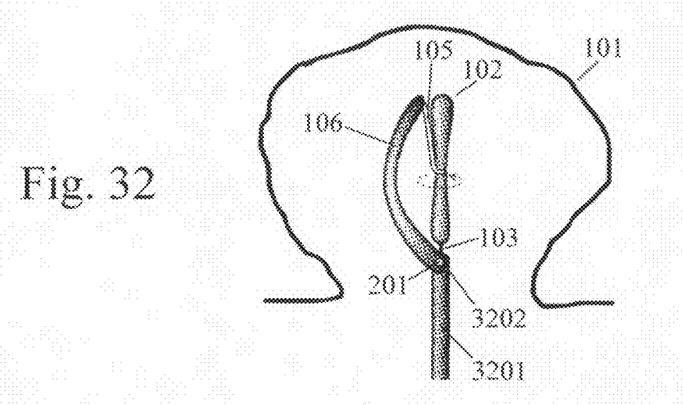
FIG. 32 shows the first stage, before the spool has been rotated.
Figure 33:
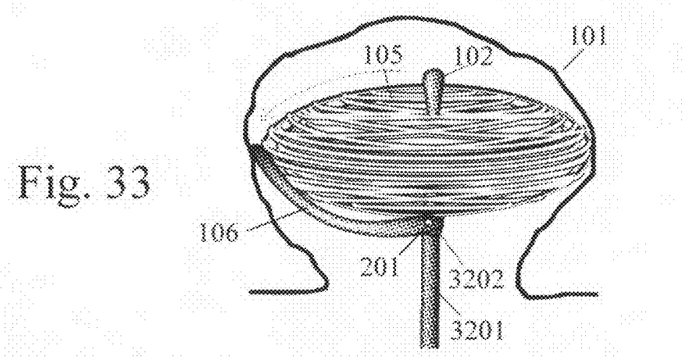
FIG. 33 shows the second stage, after the spool has been rotated, but before the catheter has been withdrawn.
Figure 34:
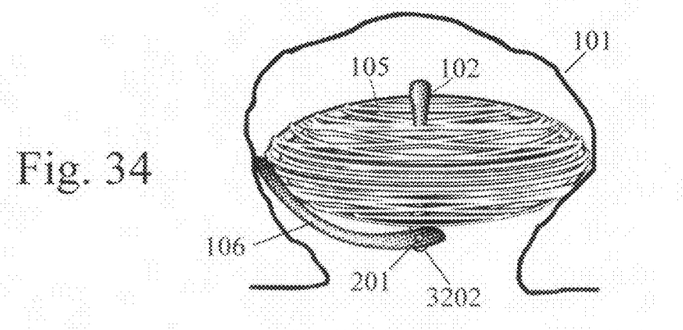
FIG. 34 shows the third stage, after the catheter has been withdrawn.
Figure 35:
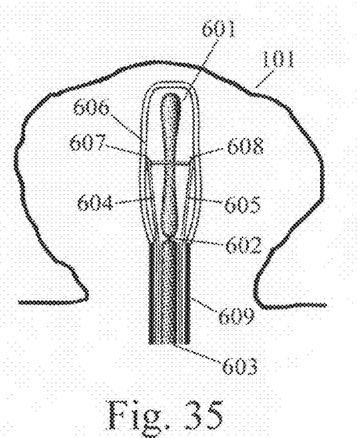
FIGS. 35 through 38 show an example, with four stages of deployment, that is similar to the example that was originally shown in FIGS. 6 through 9, except that now the inflatable guide loop can be deflated, detached from the catheter, and left behind in the aneurysm when the catheter is removed from the body.
Figure 36:
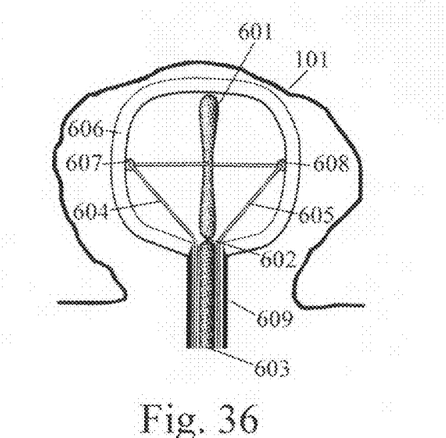
Figure 37:
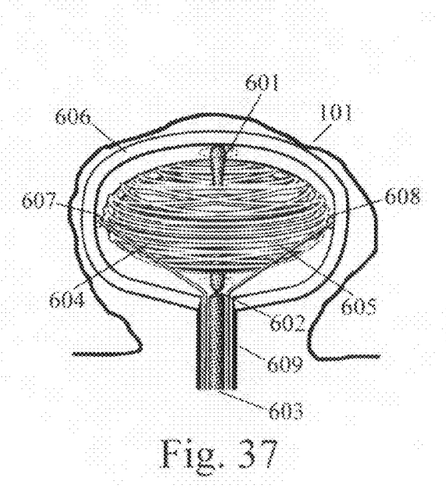
Figure 38:
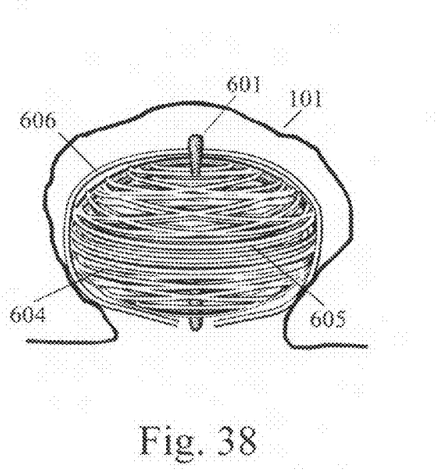

FIGS. 32-34 show another example of the invention. This example is similar to the example that was originally shown in FIGS. 1 through 5, except that now the guide arm 106 is detached from the catheter and left behind in the aneurysm when the catheter is removed from the body. Detachment of the guide arm in this manner can allow rotational accumulation of a larger embolizing mass within the aneurysm without causing trauma to the aneurysm wall when the catheter is removed. In this example, there is a detachable section 3202 at the distal end of catheter 3201 and guide arm 106 pivots on this detachable section.

FIG. 32 shows this example in the first stage of deployment wherein spool 102, filament 105, and guide arm 106 have been inserted into aneurysm 101, but spool 102 has not yet been rotated. FIG. 33 shows this example in the second stage of deployment wherein spool 102 has been rotated repeatedly, winding filament 105 around spool 102 in order to form a filament disk that largely fills the width of the aneurysm; and guide arm 106 has pivoted outwards as winding filament 105 has accumulated around spool 102. FIG. 34 shows the final stage of deployment wherein detachable section 3202 has been detached from catheter 3201 and catheter 3201 has been removed from the body.

FIGS. 35-38 show another example of this invention. This example is similar to the example that was originally shown in FIGS. 6 through 9, except that now the inflatable guide loop 606 can be deflated, detached from the catheter, and left behind in the aneurysm when the catheter is removed from the body. Detachment of the inflatable guide loop this manner can allow rotational accumulation of a larger embolizing mass within the aneurysm without causing trauma to the aneurysm wall when the catheter is removed.

In this example, at least one longitudinal flexible member adheres or otherwise attaches to itself as it winds around the at least one core member in order to prevent the longitudinal flexible member from unraveling after winding. In various examples, aneurysms with different shapes and sizes may be optimally filled by varying the number, length, shape, detachment points, and/or material of the at least one core member and the at least one longitudinal flexible member.

Further, in various examples, the timing of rotation may be coordinated with the timing of the diastolic phase of blood circulation in order to reduce stress on the aneurysm wall during rotation. For example, the central core member may be rotated only during the low pressure phase in order to minimize stress on the aneurysm wall. Restricting rotation of the core member and/or longitudinal flexible member to the diastolic phase of blood circulation can help to avoid having both pushing forces and sheering forces operating against the walls of the aneurysm at the same time.

We claim:
1. A device to treat an aneurysm comprising:
at least one core member including a distal end, that is inserted into the aneurysm; and at least one longitudinal flexible member, wherein the longitudinal flexible member is attached to the core member, wherein the longitudinal flexible member is wound with multiple complete rotations around the at least one core member within the aneurysm, wherein the device is in a first state prior to insertion of the core member into the aneurysm wherein the longitudinal flexible member is wound a first number of complete rotations around the core member and this first number can be zero, wherein the device is in a second state after insertion of the core member into the aneurysm wherein the longitudinal flexible member is wound a second number of complete rotations around the core member and this second number is greater than the first number, and wherein accumulation of the at least one longitudinal flexible member within the aneurysm reduces blood flow into the aneurysm; and
a guide loop that guides the longitudinal flexible member as the longitudinal flexible member winds around the core member and that encircles the core member, including the distal end of the core member, in a plane which is substantially parallel to the rotational axis of the core member while the longitudinal flexible member winds around the core member.

2. The device in claim 1 wherein the at least one longitudinal flexible member is wound repeatedly around the at least one core member by one or more rotations selected from the group consisting of: rotation of the at least one core member; and rotation of the longitudinal flexible member around the core member.

3. The device in claim 1 wherein the at least one longitudinal flexible member passes through at least one guiding structure to guide the longitudinal flexible member as it winds repeatedly around the core member and wherein the at least one guiding structure is selected from structures in the group consisting of: an arm, a wire, a cable, a catheter, a rod, a loop, a balloon, and a structure with shape memory.

4. The device in claim 1 wherein the at least one core member has a shape selected from the group consisting of: cylinder with rounded ends, figure-eight, hour glass, torus, ellipse, oval, sphere, cube, and fork with rounded prongs.

5. The device in claim 1 wherein the at least one longitudinal flexible member is selected from the group consisting of: biocompatible thread, biocompatible string, biocompatible filament, biocompatible tape, biocompatible wire, biocompatible coil, and string of connected biocompatible members.

6. The device in claim 1 wherein the at least one longitudinal flexible member adheres or otherwise attaches to itself as it winds around the at least one core member in order to prevent the longitudinal flexible member from unraveling after winding.

7. The device in claim 1 wherein the at least one longitudinal flexible member winds around a core member with a rotational axis with an orientation that is selected from the group consisting of: substantially perpendicular to the plane of the aneurysm neck; and substantially parallel to the plane of the aneurysm neck.

8. The device in claim 1 wherein aneurysms with different shapes and sizes can be optimally filled by varying the number, length, shape, detachment points, and/or material of the at least one core member and the at least one longitudinal flexible member.

9. A device to treat an aneurysm comprising:
at least one core member including a distal end, that is inserted into the aneurysm; and at least one longitudinal flexible member, wherein the longitudinal flexible member is attached to the core member, wherein the longitudinal flexible member is wound with multiple complete rotations around the at least one core member within the aneurysm, wherein the device is in a first state prior to insertion of the core member into the aneurysm wherein the longitudinal flexible member is wound a first number of complete rotations around the core member and this first number can be zero, wherein the device is in a second state after insertion of the core member into the aneurysm wherein the longitudinal flexible member is wound a second number of complete rotations around the core member and this second number is greater than the first number, wherein the longitudinal flexible member accumulates around the core member in an outwardly-expanding manner, and wherein accumulation of the at least one longitudinal flexible member within the aneurysm reduces blood flow into the aneurysm, and wherein the at least one longitudinal flexible member is wound repeatedly around the at least one core member by one or more rotations selected from the group consisting of: rotation of the at least one core member; and rotation of the longitudinal flexible member around the core member; and
a guide loop that guides the longitudinal flexible member as the longitudinal flexible member winds around the core member and that encircles the core member, including the distal end of the core member, in a plane which is substantially parallel to the rotational axis of the core member while the longitudinal flexible member winds around the core member.

10. The device in claim 9 wherein the at least one longitudinal flexible member passes through at least one guiding structure to guide the longitudinal flexible member as it winds repeatedly around the core member and wherein the at least one guiding structure is selected from structures in the group consisting of: an arm, a wire, a cable, a catheter, a rod, a loop, a balloon, and a structure with shape memory.

11. The device in claim 9 wherein the at least one core member has a shape selected from the group consisting of: cylinder with rounded ends, figure-eight, hour glass, torus, ellipse, oval, sphere, cube, and fork with rounded prongs.

12. The device in claim 9 wherein the at least one longitudinal flexible member adheres or otherwise attaches to itself as it winds around the at least one core member in order to prevent the longitudinal flexible member from unraveling after winding.

13. The device in claim 9 wherein the at least one longitudinal flexible member winds around a core member with a rotational axis with an orientation that is selected from the group consisting of: substantially perpendicular to the plane of the aneurysm neck; and substantially parallel to the plane of the aneurysm neck.

* * * * *